United States Patent [19]

Kline

[11] 4,365,631

[45] Dec. 28, 1982

[54] FLOWABLE SUBSTANCE APPLICATOR

[76] Inventor: Larry H. Kline, 18 Broad St., Suite 805, Charleston, S.C. 29401

[21] Appl. No.: 300,027

[22] Filed: Sep. 8, 1981

[51] Int. Cl.³ .............................................. A61M 3/00
[52] U.S. Cl. .................................. 128/235; 128/261; 128/271
[58] Field of Search ................................ 128/260–271, 128/235, 239, 242, 245

[56] References Cited

U.S. PATENT DOCUMENTS

| | | | |
|---|---|---|---|
| 942,590 | 12/1909 | Sanborn . | |
| 1,101,017 | 6/1914 | Feltmann . | |
| 1,258,979 | 3/1918 | Beard | 128/261 |
| 1,640,928 | 8/1927 | Donovan | 128/271 |
| 1,809,558 | 6/1931 | Loeble | 128/271 |
| 2,512,713 | 6/1950 | Cahill | 128/DIG. 30 |
| 2,683,456 | 7/1954 | Pierson | 128/239 |
| 2,974,666 | 3/1961 | Coumbis et al. | 128/271 |
| 3,044,467 | 7/1962 | Campau | 128/DIG. 30 |
| 3,104,665 | 9/1963 | Towns | 128/271 |
| 3,882,866 | 5/1975 | Zackheim | 128/235 |

*Primary Examiner*—C. Fred Rosenbaum
*Attorney, Agent, or Firm*—Larry Harold Kline

[57] ABSTRACT

A device and method are disclosed for holding a flowable substance and applying the flowable substance to an orifice of a body comprising a nozzle, a plunger section, and a void area, with the void area sized and shaped to fit between the nozzle and the plunger section, wherein the nozzle is placed into the orifice and the plunger section pressed in order to force the flowable substance through a plurality of openings in the nozzle into the orifice.

51 Claims, 12 Drawing Figures

FLOWABLE SUBSTANCE APPLICATOR

This invention relates to an applicator apparatus and more particularly to an apparatus which can be worn by a person.

Constipation, diarrhea, pregnancy and overexertion are common physical causes of hemorrhoids. Certain occupations that require continued standing or sitting also contribute to that condition. Most hemorrhoidal flare-ups are minor and may last for several days and can be self-treated. Presently, hemorrhoidal conditions are treated by the use of cream or suppositories. The cream may be placed or injected into the anus. Hemorrhoids are internal or external varicose veins in the anal or rectal area. When these veins become swollen or irritated, pain results. The treatment by cream tends to lubricate the anal region reducing irritation and helping make bowel movements less painful. Creams may also give comfort for the pain, itching, and discomfort of external and internal hemorrhoids, proctitis, papillitis, cryptitis, anal fissures, incomplete fistulas, pruritus ani and the relief of local pain and discomfort following anorectal surgery. One of the many problems that individuals have is that they must continue to work and function when suffering the discomforts of the above problems. The present invention provides a device and method for relieving the discomfort in a person who must continue to function despite an uncomfortable medical problem in the anal region.

An object of the present invention is to provide a device which can hold a supply of cream to be applied in the anal region at a time desired by the user.

Another object of the present invention is to provide a device which can be activated to supply cream to the anal region without removal of the device.

A further object of the present invention is to provide an applicator section of a device which can be activated to supply cream, ointment, or liquid to the anal or vaginal region of the body, which may be stored in that area of the body until the desired use, or which may be utilized to apply the cream, ointment, or liquid without the touching of the cream, ointment, or liquid by the user.

Still another object of the present invention is to provide a device which can be worn by a person and which carries a supply of cream which may be applied to the anal region.

A further object of the present invention is to provide a device which is shaped to be comfortably worn and held in the anal region of a person.

Another object of the present invention is to provide a device which extends internally into the anal region of a person and which may be worn during the normal daily functions of a person.

Still another object of the present invention is to provide a device, which can supply cream in the anal region of a person at a desired time, which is disposable.

A further object of the present invention is to provide a device, which can provide cream in the anal region of a person, which is re-usable.

Another object of the present invention is to provide means to re-fill a region within a device with cream which may be later applied to the anal region of a person.

Still another object of the present invention is to provide a device which may hold a supply of cream which may be applied to the anal region of a person which may be held onto the anal region of a person by a variety of means.

A further object of the present invention is to provide a device which may hold a supply of cream which may be applied to the anal region of a person which may be held onto the anal region by a plurality of straps.

Another object of the present invention is to provide a device, which may hold a supply of cream and which may be held onto the anal region by adhesive material, which may adhere to garments.

Still another object of the present invention is to provide a device which may hold a supply of cream, ointment, or liquid and which may be held onto the anal region or vaginal region by adhesive material which adheres directly to the body of the user.

A further object of the present invention is to provide a device which can be worn by a person and extends internally into the anal region, thereby separating the inner sides of the anal region and any internal hemorrhoids which might have been in contact had the device not been placed therein.

Another object of the present invention is to provide a device which can be worn by a person and has an external portion, which may be lubricated, which may separate external hemorrhoids which extend from the anal region of a person and might be in contact without the device being utilized.

These and other objects and features of the invention will be apparent from the following description and appended claims.

Briefly, the invention is a device and method for holding a flowable substance and applying the flowable substance to an orifice of a body. The device comprises an applicator section. The application section comprises a nozzle which is sized and shaped to fit within the orifice of the body. The nozzle has a base, an elongated section, a tip, and a plurality of openings. The plunger section is sized and shaped to fit within the nozzle. The plunger section extends from the base of the nozzle towards the tip of the nozzle. A void area is sized and shaped to fit between the nozzle and the plunger section. The void area is operative to hold the flowable substance.

When the nozzle is placed in the orifice and the plunger section is pressed toward the tip of the nozzle, the flowable substance will be forced from the void area, through the plurality of openings in the nozzle, and out from the device into the orifice.

A support section is secured to the applicator section. The support section supports the applicator section. The plunger section may be pressed through an opening in the support section. The base of the nozzle is sloped toward the support section and is secured to the support section.

The plurality of openings comprises a plurality of openings in the base. The plurality of openings further comprises a plurality of openings in the elongated section and an opening in the tip.

Securing means is operative to hold the support section at a desired portion of the body so that the nozzle is held in the orifice. The securing means may comprise an applicator apparatus secured around the body and operative to hold the support section within the applicator apparatus. The securing means may comprise adhesive means secured to the outer portion of the support section. The securing means may comprise adhesive means secured to the inner portion of the support section.

The device may further comprise a packet, sized and shaped to fit into the void area between the nozzle and the plunger section. The packet is operative to hold the flowable substance.

A sheath, sized and shaped to fit over the nozzle, may be utilized to cover all of the plurality of openings in the nozzle. Sheath securing means may be connected to the support section to secure the sheath onto the nozzle. A pressure ridge may be secured onto the support section to relieve pressure.

The elongated section is sloped downward from the tip of the nozzle to the base of the nozzle. The nozzle may be permanently secured to the support section in the area where the base of the nozzle meets the support section. The nozzle may be removably secured to the support section in the area where the base of the nozzle meets the support section.

The nozzle may further comprise a nozzle opening with a nozzle removal cover through which the flowable substance may be placed into the void area. The sheath may comprise a sheath opening with a sheath removable cover through which the flowable substance may be placed. The sheath opening fits over the nozzle opening and the flowable substance may be placed through the sheath opening and the nozzle opening into the void area by a flow dispensing means. The flow dispensing means may be a tube containing the flowable substance. The nozzle opening and the sheath opening may be grooved openings. The flow dispensing means may be screwed into the grooved openings to secure the flow dispensing means in the sheath opening and the nozzle opening when the flowable substance is placed into the void area.

The nozzle removal cover for the nozzle opening may have a slotted top which can be turned with pressure applied thereto. The sheath removal cover for the sheath opening may have a slotted top which can be turned with pressure applied thereto.

A support section is sized and shaped to fit so that nozzle enters the desired orifice of the body, with the support section fitting onto the appropriate section of the body without projecting outward away from the body.

The method for applying a flowable substance to an orifice of the body comprises placing the flowable substance into a device with an applicator section comprising a nozzle, a plunger section, and a void area. The method also comprises inserting the nozzle of the applicator section into the orifice and pressing the plunger section toward the tip of the nozzle. The flowable substance in the void area is then pressed from the void area and through the plurality of openings in the nozzle and out from the device into the orifice. The method may further comprise wearing the device on the body after placing the flowable substance into the device and prior to pressing the plunger section. At the desired time, the plunger section may be pressed and the flowable substance applied to the orifice of the body.

The invention will be more fully understood from the following detailed description and appended claims when taken with the drawings in which:

Figure 1:
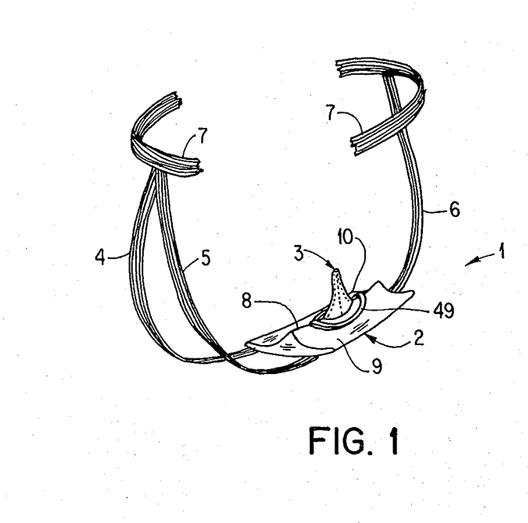
FIG. 1 is an isometric view of applicator section 3 secured onto applicator support section 2, which is secured within applicator apparatus 1.

Referring now to the drawings, FIG. 1 is an isometric view of applicator section 3 secured onto applicator support section 2, which is secured within applicator apparatus 1. Applicator apparatus 1 may be any type of apparatus which can hold the applicator support section 2 in place where the applicator section 3 extends into the anal or vaginal region of a person. The applicator apparatus 1 is shown with a waist band 7 which would extend around the person. A pressure relieving ridge 49 extends around the interior of support section 2 in order to relieve pressure in the anal region.

Front support straps 4 and 5 and rear support strap 6 would extend between the legs of a person in order to hold the applicator support section 2 in place. The applicator apparatus 1 may be utilized for males or females. The front support straps 4 and 5 are designed to fit in a manner so as not to disturb the male or female organs.

Support section 2 is designed to fit into the cavity region where the lobes of the buttocks of a person come together at the anal region. The support section 2 may be designed in any fashion so as to comfortably fit between the buttocks and into the anal region of a male or female.

Applicator section 3 extends into the anus in this illustration, but could also extend into the vagina of a female, if desired. The applicator section 3 may be lubricated prior to placing the section 3 into the anus or vagina of a person. The Applicator support section 2 may have a separating ridge 8 which fits into the deepest area of the crevice between the buttocks of a person, with separating sides 9 and 10 on either side of separating ridge 8.

Figure 2:
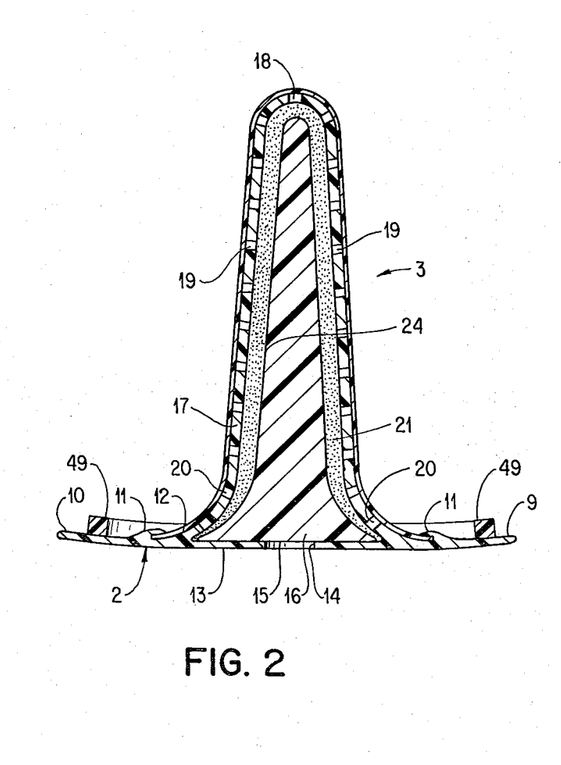
FIG. 2 is a lateral sectional view showing an illustrative internal view of applicator section 3, with applicator section 3 being a disposable-type applicator.

FIG. 2 is a lateral sectional view showing an illustrative internal view of applicator section 3, with applicator section 3 being a disposable-type applicator.

This device in the present invention may be made for a disposable-type applicator or may be made for an applicator which may be re-usable. FIG. 2 shows a disposable-type applicator.

The applicator section 3 has within it an applicator plunger 16. The applicator section 3 has an applicator nozzle 17 containing a plurality of side openings 19, a plurality of base openings 20, and a single tip opening 18. Applicator section 3 may be made of a flexible material for the comfort of the person wearing the device 1 or may be made of any material which will perform the functions of applicator section 3 herein.

Sheath 12 may be secured over the applicator nozzle 17 in order to protect and keep clean nozzle 17, single tip opening 18, and the plurality of openings 19 and 20 therein. Sheath 12 may be secured in any manner to the applicator section 3 or applicator support section 2. The sheath 12 is shown held down by a sheath hold-down snap ring 11. When in use, the sheath 12 is removed and the applicator section 3 is inserted into the anal or vaginal areas with the applicator nozzle 17 extending into the anus or vagina of a person.

At the desired time when the person using the device requires additional relief, the person may press the applicator plunger 16 at pressing area 15. The applicator plunger 16 will be pressed against the area within the application section 3 within which cream or flowable substance packet 21 is located. Cream of flowable substance packet 21 will burst from the pressure of the pressed applicator plunger 16 and the cream or flowable substance within cream or flowable substance packet 21 will be forced out of the plurality of nozzle openings 19 and 20 and the single tip opening 18 through the applicator nozzle 17 to the outer portion of applicator section 3 and against the inner and side portions of the anal or vaginal region of the user. The cream or flowable substance packet 21 shown in FIG. 2 and FIG. 3 may be any type of packaging for the flowable substance, such as a cream, ointment, or liquid, which can be located in the region between the applicator plunger 16 and the applicator nozzle 17. In fact, the flowable substance, such as a cream, ointment or liquid, may simply be placed in that area without packaging, if desired.

The disposable-type applicator section 3 may be worn as long as desired and then disposed of appropriately. The disposable-type applicator section 3 may be permanently secured to an applicator support section 2, which is also disposed of, or may be removable from the applicator support section 2, which might be re-usable with a new disposable-type applicator section 3. The applicator support section 2 may be permanently secured to an apparatus, such as apparatus 1, or may be secured in a removable manner so that a new applicator support section 2 and applicator section 3 may be utilized with the same applicator apparatus 1. As noted herein, the applicator support section 2 may be secured to the person in a variety of ways, not only in the manner shown in FIG. 1, which utilizes applicator apparatus 1.

Pressing area 15 is located in an opening 14 in base 13 of applicator support section 2.

Figure 3:
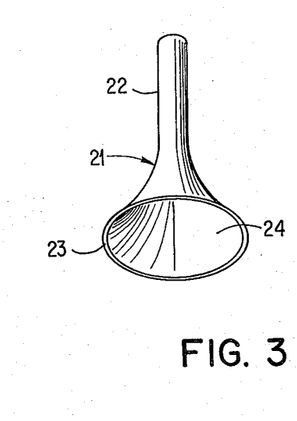
FIG. 3 is an isometric view of cream packet 21, a cross-section of which is shown in FIG. 2.

FIG. 3 is a isometric view of cream or flowable substance packet 21, a cross-section of which is shown in FIG. 2. The shape of cream packet 21 shown in FIG. 3 is such that it would fit snugly within the region between the applicator plunger 16 and applicator nozzle 17 prior to the time that pressing area 15 is pressed. Cream packet 21 may be of a different shape, if desired, as may also be the applicator plunger 16 and the applicator nozzle 17. Ideally, the cream packet 21 would fit snugly between the applicator plunger 16 and the applicator nozzle 17 so as to increase the efficiency of the device and for maximum utilization of the cream, ointment, or liquid. If desired, the cream packet 21 may not be used, but cream, ointment, or liquid may simply be inserted into the cavity between the applicator plunger 16 and the applicator nozzle 17.

Cream packet 21 is shown having a shaft 22 and a base 23, with an interior section 24.

Figure 4:
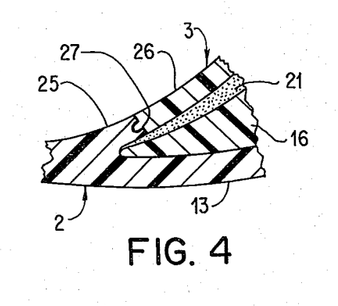
FIG. 4 is a partial sectional view through applicator section 3 showing the removable applicator nozzle 26, when the applicator section 3 is designed for re-use.

FIG. 4 is a partial sectional view through applicator section 3 showing the removable applicator nozzle 26, when the applicator section 3 is designed for re-use.

Removable applicator nozzle 26 is shown snapped into the top portion 25 of applicator support section 2 by use of a securing section 27 of removable applicator nozzle 26. The applicator plunger 16 is similar in either the disposable-type applicator or the re-usable-type applicator. The cream or flowable substance packet 21 or the cream or flowable substance area 21 is similarly located in either the disposable-type or the re-usable type applicator.

Figure 5:
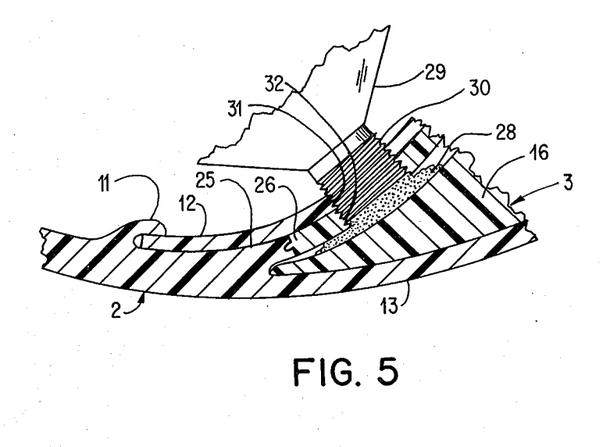
FIG. 5 is a partial sectional view through applicator section 3 showing the applicator section 3 being refilled with cream 28 from cream dispenser 29.

FIG. 5 is a partial sectional view through applicator section 3 showing the applicator section 3 being refilled with cream or flowable substance 28 from cream or flowable substance dispenser 29.

When re-using the re-usable applicator section 3, a cream packet, such as cream packet 21, may be utilized or cream, ointment, or liquid may be inserted into the appropriate cavity by any appropriate manner.

FIG. 5 shows one method of filling the cavity between removable applicator nozzle 26 and applicator plunger 16 with cream, ointment, or liquid.

In the design in FIG. 5, the sheath 12, which is secured within sheath hold-down snap ring 11, is secured over the removable applicator nozzle 26 so that none of the flowable substance, such as cream, ointment, or liquid, being placed into the cavity between removable applicator nozzle 26 and applicator plunger 16 will be able to come out of the single tip opening 18 or the plurality of nozzle openings 19 and 20 within the removable applicator nozzle 26.

Cream or flowable substance dispenser 29 is shown with threaded portion 30. The threaded portion 30 of cream dispenser 29 is screwed into the threaded opening 31 in sheath 12 and into threaded opening 32 in removable applicator nozzle 26. The flowable substance dispenser 29 is activated and the flowable substance 28 enters the void area between the removable applicator nozzle 26 and the applicator plunger 16.

Figure 6:
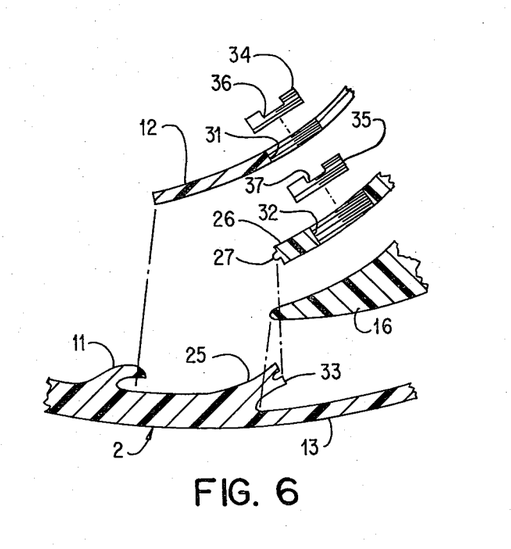
FIG. 6 is an exploded partial sectional view of FIG. 5.

FIG. 6 is an exploded partial sectional view of FIG. 5. In FIG. 6, plug 34 which secures within sheath 12, and plug 35 which secures within removable applicator nozzle 26 are shown. Plug 34 has a coin slot 36 in which a small coin or other similarly-shaped object may be utilized to remove the plug 34 from sheath 12. Plug 35 has a coin slot 37 in which a small coin or other similarly-shaped object may be utilized to remove the plug 35 from removable applicator nozzle 26.

Top portion 25 of applicator support section 2 has a securing section 33 in which the securing section 27 of removable applicator nozzle 26 fits. Sheath 12 secures down by snap ring 11.

Figures 7, 8, 9:
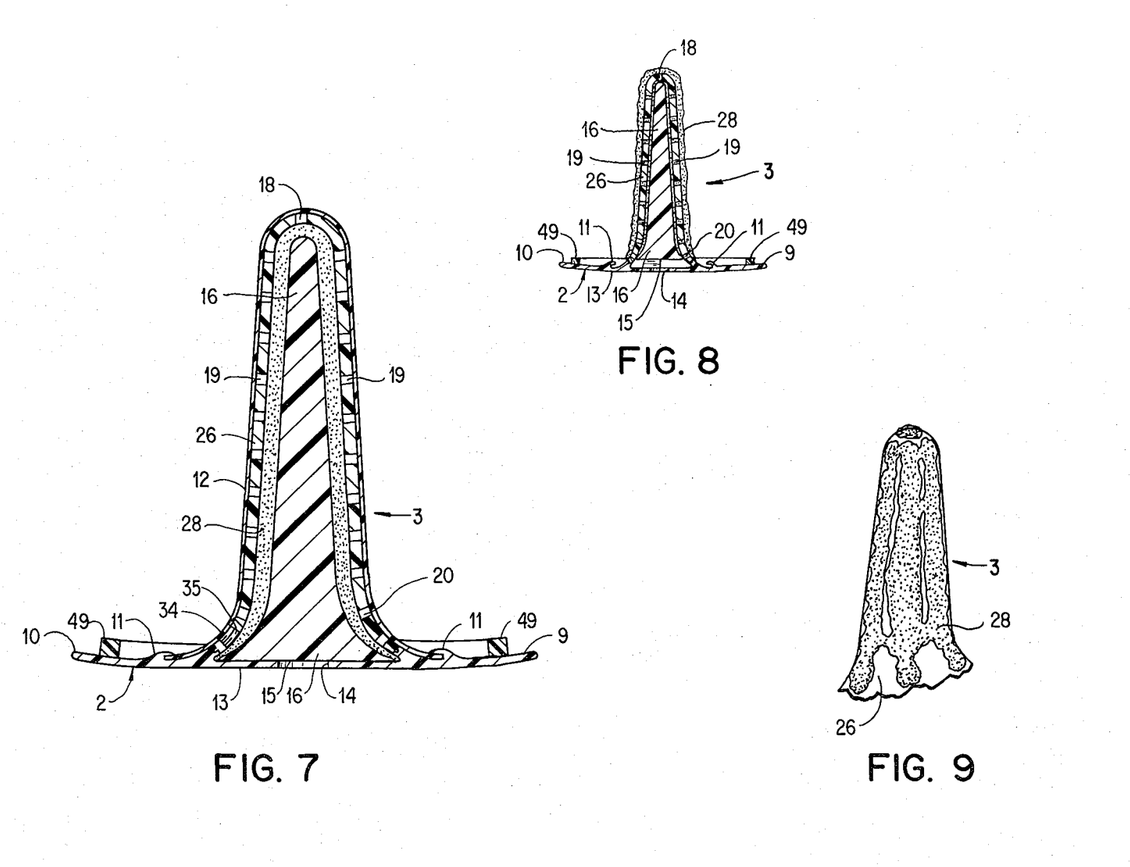
FIG. 7 is a lateral sectional view showing an internal view of applicator section 3 with the applicator section 3 being a re-usable-type applicator and sheath 12 being secured thereon.
FIG. 8 is a lateral sectional view showing an internal view of applicator section 3 with applicator plunger 16 being pressed forward and the cream or flowable substance 28 being pushed through single tip opening 18 and the plurality of nozzle openings 19 and 20 in removable applicator nozzle 26.
FIG. 9 is an isometric view of the applicator section 3 with cream or flowable substance 28 having been pushed through the single tip opening 18 and the plurality of nozzle openings 19 and 20 in removable applicator nozzle 26.

FIG. 7 is a lateral sectional view showing an internal view of applicator section 3 with the applicator section 3 being a re-usuable-type applicator and sheath 12 being secured thereon. In order to clean the re-usable applicator section 3, the sheath 12 may be removed, the removable applicator nozzle 26 may be removed, and the remainder of the applicator 3 may be cleaned. Then, if a cream packet 21 is desired for use, it may be placed against the applicator plunger 16 and the removable applicator nozzle 26 secured back onto the device 1. The sheath 12 can then be snapped on and the device 1 is ready for use.

FIG. 8 is a lateral sectional view showing an internal view of applicator section 3 with applicator plunger 16 being pressed forward and the cream or flowable substance 28 being pushed through single opening 18 and the plurality of openings 19 and 20 in removable applicator nozzle 26. The removable applicator nozzle 26 will have any desired plurality of side openings 19 and base openings 20 and could possibly have more than one opening at the tip of the removable applicator nozzle 26 in lieu of single tip opening 18.

The plurality of side openings 19 would allow cream or flowable substance 28 to be placed into the inner region of the anus or vagina in order to soothe and combat problems associated with those areas of the body, one of which might be internal hemorrhoids in the anal region. The cream or flowable substance 28 extending through the plurality of base openings 20 may help in soothing and treating problems of the outer region of the anus or vagina, one such problem of the anal region being external hemorrhoids.

FIG. 9 is an isometric view of the applicator section 3 with cream or flowable substance 28 having been pushed through the single tip opening 18 and the plurality of nozzle openings 19 and 20 in removable applicator nozzle 26.

In FIG. 9, the pressing area 15 of applicator plunger 16 has been pressed, causing the cream or flowable substance 28 to extend through the single tip opening 18 and the plurality of openings 19 and 20 as it would be when the device 1 is in use in the anal or vaginal region of a person.

Figure 10:
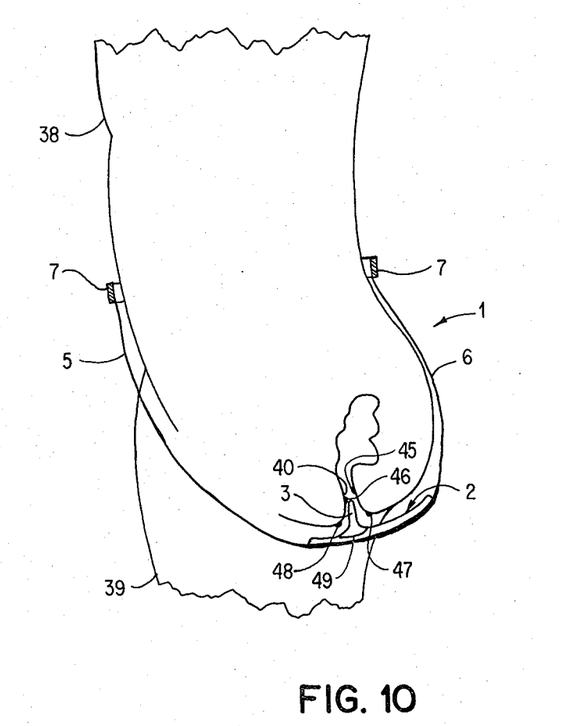
FIG. 10 is a side elevational view of a human body with the applicator section 3 supported on the applicator support section 2 which is secured to applicator apparatus 1, which is loosely applied therein.

FIG. 10 is a side elevational view of a human body with the applicator section 3 supported on the applicator support section 2 which is secured to applicator apparatus 1, which is loosely applied therein.

The human body is shown having a body trunk 38 showing one leg 39, anal opening 40, and waist band 7 with supporting straps 5 and 6 of apparatus 1. Applicator section 3 is illustratively shown separating internal hemorrhoids 45 and 46 and external hemorrhoids 47 and 48.

In use, the applicator section 3 may be lubricated and will reduce the friction between hemorrhoidal areas by its presence as well as by the soothing cream, ointment, or liquid with which it is coated and/or contains. The applicator section 3 may be lubricated prior to use by the use of any lubricant, such as K-Y Jelly, or by the application of a cream, ointment, or liquid similar or the same as the cream, ointment, or liquid which is stored within the applicator section 3. The applicator section 3 can be placed near the anal or vaginal region dry, with the cream, ointment or liquid pressed out of the applicator section 3 simultaneously with the insertion. The device may be utilized so that the user does not have to touch the cream, ointment, or liquid being utilized.

Figure 11:
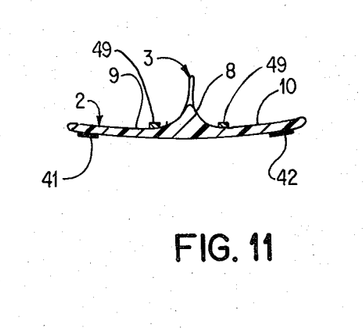
FIG. 11 is a lateral sectional view showing adhesive strips 41 and 42 secured to the outer portion of applicator section 2 in order to adhere to the undergarments of a person to hold the applicator section 3 and the applicator support section 2 in place.

FIG. 11 is a lateral sectional view showing adhesive strips 41 and 42 secured to the outer portion of applicator section 2 in order to adhere to the undergarments of a person to hold the applicator section 3 and the applicator support section 2 in place.

A plurality of adhesive strips, such as 41 and 42, may be utilized or one large adhesive strip may be utilized in order to secure the applicator section 2 to the undergarment. The holding means to secure the applicator section 2 to the undergarment may be any desired holding means, depending upon the choice of the user or the manufacturer of the device.

Figure 12:
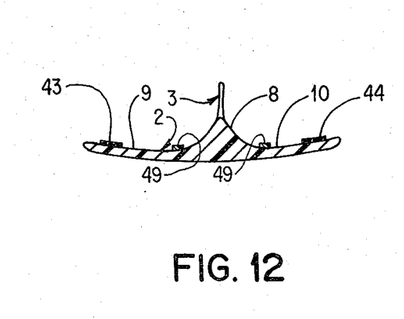
FIG. 12 is a lateral sectional view showing adhesive strips 43 and 44 secured to the inner portion of applicator section 2 in order to adhere to the body of a person utilizing the device 1.

FIG. 12 is a lateral sectional view showing adhesive strips 43 and 44 secured to the inner portion of applicator section 2 in order to adhere to the body of a person utilizing the device 1.

A plurality of adhesive strips, such as 43 and 44, may be utilized to secure the applicator section 2 to the body of a person. Any type of holding means desired by the user or the manufacturer may be utilized to secure the applicator section 2 in the appropriate areas, as desired.

This invention provides a device which can be either disposable or re-usable. When needed, the device can be re-filled with a flowable substance for future use. The device can store a supply of flowable substance and can be shaped to be comfortably worn and held in the anal or vaginal region of the body during the normal daily functions of a person. The device may be held onto the anal or vaginal regions of the body by a variety of means, including straps, or adhesive material which will adhere either to the undergarments of the person or the body of the person. The device can separate the inner and outer sides of the anal or vaginal region which might have been in contact had the device not been placed therein. The device can be activated, as desired by the user wearing the device, without having to remove the device from the body. The device allows the user, who is experiencing problems in the anal or vaginal region of the body, to treat those problems with a flowable substance, such as a cream, ointment, or liquid, without having to touch that flowable substance. The device may be lubricated prior to being utilized, or may be lubricated by the activation of the device at the time of utilization.

The present invention provides a device and method for relieving the discomfort in a person who must continue to function despite an uncomfortable medical problem in the anal or vaginal region of the body. Many persons, who have to continue to work and function, even when suffering discomforts in the anal or vaginal region, can utilize the present invention to give comfort throughout the day. A businessman or lady in their business clothing can, by use of the present applicator device, supply relief to the tender area without touching the cream being used and without the risk of spoiling their appearance or clothing.

Many vaginal or rectal disorders may require the use of a cream, ointment, or liquid. Frequently, this cream, ointment, or liquid must be applied several times a day. Whether the invention is disposable or re-usable, it allows the user the option of inserting the device into the vaginal or rectal area, activating the device for treatment, and removing the device immediately; or the user may insert the device and wear it continuously, activating the device when needed. Therefore, even though the device can provide immediate relief, it can also provide continued relief, whichever is desired by the user. If the device is re-usable, it may be used, cleaned, and then refilled with a flowable substance for future use.

The applicator plunger 16 is of similar shape and size as the disposable applicator nozzle 17 or the re-usable applicator nozzle 26. The applicator nozzle 17 is similar in shape and size to the re-usable applicator nozzle 26. The applicator nozzle 17 and 26 may be of flexible material so as to move appropriately when being pressed in certain areas by the applicator plunger 16 in order to dispense the flowable substance, and for ease and comfort within the orifice region of the user. It is desirable that the applicator plunger be of similar shape and size as the applicator nozzle so that all of the flowable substance, which is stored within the device, may be pressed out of the device through the plurality of openings in the nozzle. The applicator section 3 may be flexible in the area closest to the applicator support section 2 so that when the applicator plunger 16 is pressed upward, the base area of the applicator section 3 will allow some movement in order to extract the maximum amount of flowable substance through the plurality of openings in the nozzle.

As shown in FIG. 1, the support section 2 of the device is shaped to fit into the pertinent area of the body. The device in FIG. 1 is shown sloped to fit appropriately into the anal region of the body. If the vaginal region of the body were being utilized, the support section could be shaped to fit that section of the body. The thickness of the support section depends on the desire of the user or manufacturer. As shown in FIG. 2, the support section need only be thick enough to provide the desired support.

The applicator nozzle is sized and shaped to fit within the desired orifice of the body. The nozzle has a sloped base, an elongated section, a tip, and a plurality of openings. There is a plurality of openings 20 in the sloped base and a plurality of openings 19 in the elongated section. The elongated section is referred to in this application as the applicator nozzle 17 in the disposable version of the invention and as the applicator nozzle 26 in the re-usable version of the invention.

The present invention may be utilized for human beings, but might also be applicable for use in veterinary medicine to aid and relieve problems occurring in various animals.

A ridge 49 on support section 2 relieves pressure that might occur in the covered region. The device, when worn, will not be noticed by others. Clothing will fit over the device. There are no outwardly protruding parts in the device. The entire plunger section is within the nozzle and does not protrude from the device.

While the invention has been described with reference to specific embodiments, the description is illustrative and is not to be construed as limiting the scope of the invention. Various modifications and changes may occur to those skilled in the art without departing from the spirit and scope of the invention as defined by the appended claims.

I claim:

1. A device for holding a flowable substance and applying said flowable substance to an orifice of a body comprising an applicator section comprising:
   a. a nozzle, sized and shaped to fit within said orifice of said body, with a sloped base, an elongated section, and a plurality of openings in said sloped base and said elongated section;
   b. a plunger section within said device, sized and shaped to fit within said sloped base and said elongated section of said nozzle, extending from said sloped base of said nozzle toward said tip of said nozzle; and
   c. said nozzle and said plunger section being spaced apart to form a cavity which is sized and shaped to fit between said nozzle and said plunger section from said sloped base through said elongated section, said cavity operative to hold said flowable substance,
   whereby when said nozzle is placed in said orifice and said plunger section is pressed toward said tip of said nozzle, said flowable substance will be forced from said cavity through said plurality of openings in said nozzle and out from said device into said orifice.

2. A device according to claim 1 further comprising a support section secured to and operative to support said applicator section.

3. A device according to claim 2 further comprising an opening in said support section through which said plunger section may be pressed to move said plunger section toward said tip of said nozzle.

4. A device according to claim 2 wherein said sloped base of said nozzle is sloped toward said support section and is secured to said support section.

5. A device according to claim 2 further comprising a ridge secured to the interior side of said support section and operative to relieve pressure.

6. A device according to claim 5 further comprising an opening in said support section through which said plunger section may be pressed to move said plunger section toward said tip of said nozzle.

7. A device according to claim 2 further comprising securing means operative to hold said support section at a desired portion of said body so that said nozzle is held in said orifice.

8. A device according to claim 7 wherein said securing means comprises an applicator apparatus secured around said body and operative to hold said support section within said applicator apparatus.

9. A device according to claim 7 wherein said securing means comprises adhesive means secured to the outer portion of said support section.

10. A device according to claim 7 wherein said securing means comprises adhesive means secured to the inner portion of said support section.

11. A device according to claim 1 further comprising a packet, sized and shaped to fit in said cavity between said nozzle and said plunger section, operative to hold said flowable substance,
   whereby when said nozzle is placed in said orifice and said plunger section is pressed toward said tip of said nozzle, said packet will burst and said flowable substance will be forced from said cavity through said plurality of openings in said nozzle and out from said device into said orifice.

12. A device according to claim 2 further comprising a sheath, sized and shaped to fit over said nozzle, and operative to cover all of said plurality of openings in said nozzle.

13. A device according to claim 12 further comprising sheath securing means connected to said support section and operative to secure said sheath over said nozzle.

14. A device according to claim 1 wherein said nozzle is formed from a flexible material and said elongated section is sloped downward from said tip of said nozzle to said sloped base of said nozzle.

15. A device according to claim 2 wherein said nozzle is permanently secured to said support section in the area where said sloped base of said nozzle meets said support section.

16. A device according to claim 2 wherein said nozzle is removably secured to said support section in the area where said sloped base of said nozzle meets said support section.

17. A device according to claim 1 wherein said nozzle further comprises a nozzle opening with a nozzle removable cover through which said flowable substance may be placed into said cavity.

18. A device according to claim 12 wherein said sheath comprises a sheath opening with a sheath removable cover through which said flowable substance may be placed.

19. A device according to claim 18 wherein said nozzle further comprises a nozzle opening with a nozzle removable cover through which said flowable substance may be placed into said cavity.

20. A device according to claim 19 wherein said sheath opening fits over said nozzle opening and said flowable substance may be placed through said sheath opening and said nozzle opening into said cavity by a flow dispensing means.

21. A device according to claim 20 wherein said flow dispensing means is a tube containing said flowable substance.

22. A device according to claim 20 wherein said nozzle opening and said sheath opening are grooved openings and said flow dispensing means is screwed into said grooved openings to secure said flow dispensing means in said sheath opening and said nozzle opening when said flowable substance is placed into said cavity.

23. A device according to claim 17 wherein said nozzle removable cover for said nozzle opening has a slotted top which can be turned with pressure applied thereto.

24. A device according to claim 18 wherein said sheath removable cover for said sheath opening has a slotted top which can be turned with pressure applied thereto.

25. A device according to claim 2 wherein said support section is sized and shaped to fit so that said nozzle enters the desired said orifice of said body with said support section fitting into the appropriate portion of said body without projecting outward away from said body.

26. A method for applying a flowable substance to an orifice of a body comprising:
   a. placing said flowable substance into a device with an applicator section comprising:
      (1) a nozzle, sized and shaped to fit within said orifice of said body, with a sloped base, an elongated section, and a plurality of openings in said sloped base and said elongated section;
      (2) a plunger section within said device, sized and shaped to fit within said sloped base and said elongated section of said nozzle, extending from said sloped base of said nozzle toward said tip of said nozzle; and
      (3) said nozzle and said plunger section being spaced apart to form a cavity which is sized and shaped to fit between said nozzle and said plunger section from said sloped base through said elongated section, said cavity operative to hold said flowable substance,
   b. inserting said nozzle of said applicator section into said orifice; and
   c. pressing said plunger section toward said tip of said nozzle thereby forcing said flowable substance from said cavity through said plurality of openings in said nozzle and out from said device into said orifice.

27. A method according to claim 26 further comprising securing said applicator section to a support section.

28. A method according to claim 27 wherein said device comprises an opening in said support section through which said plunger section may be pressed to move said plunger section toward said tip of said nozzle.

29. A method according to claim 26 wherein said device comprises wearing said device on said body after placing said flowable substance into said device and prior to pressing and plunger section at the desired time that said flowable substance is to be applied to said orifice of said body.

30. A method according to claim 27 wherein said sloped base of said nozzle is sloped toward said support section and is secured to said support section.

31. A method according to claim 27 wherein said device comprises a ridge secured to the interior side of said support section, said ridge operative to relieve pressure.

32. A method according to claim 31 wherein said device comprises an opening in said support section through which said plunger section may be pressed to move said plunger section toward said tip of said nozzle.

33. A method according to claim 27 wherein said device further comprises securing means operative to hold said support section at a desired portion of said body so that said nozzle is held in said orifice.

34. A method according to claim 33 wherein said securing means comprises an applicator apparatus secured around said body and operative to hold said support section within said applicator apparatus.

35. A method according to claim 33 wherein said securing means comprises adhesive means secured to the outer portion of said support section.

36. A method according to claim 33 wherein said securing means comprises adhesive means secured to the inner portion of said support section.

37. A method according to claim 26 wherein said device further comprises a packet, sized and shaped to fit in said cavity between said nozzle and said plunger section, operative to hold said flowable substance.

38. A method according to claim 27 wherein said device further comprises a sheath, sized and shaped to fit over said nozzle, and operative to cover all of said plurality of openings in said nozzle.

39. A method according to claim 38 wherein said device further comprises sheath securing means connected to said support section and operative to secure said sheath over said nozzle.

40. A method according to claim 26 wherein said nozzle is formed from a flexible material and said elongated section is sloped downward from said tip of said nozzle to said sloped base of said nozzle.

41. A method according to claim 27 wherein said nozzle is permanently secured to said support section in the area where said sloped base of said nozzle meets said support section.

42. A method according to claim 27 wherein said nozzle is removably secured to said support section in the area where said sloped base of said nozzle meets said support section.

43. A method according to claim 26 wherein said nozzle further comprises a nozzle opening with a nozzle removable cover through which said flowable substance may be placed into said cavity.

44. A method according to claim 38 wherein said sheath comprises a sheath opening with a sheath removable cover through which said flowable substance may be placed.

45. A method according to claim 44 wherein said nozzle further comprises a nozzle opening with a nozzle removable cover through which said flowable substance may be placed into said cavity.

46. A method according to claim 45 wherein said sheath opening fits over said nozzle opening and said flowable substance may be placed through said sheath opening and said nozzle opening into said cavity by a flow dispensing means.

47. A method according to claim 46 wherein said flow dispensing means is a tube containing said flowable substance.

48. A method according to claim 46 wherein said nozzle opening and said sheath opening are grooved openings and said flow dispensing means is screwed into said grooved openings to secure said flow dispensing means in said sheath opening and said nozzle opening when said flowable substance is placed into said cavity.

49. A method according to claim 47 wherein said nozzle removable cover for said nozzle opening has a slotted top which can be turned with pressure applied thereto.

50. A method according to claim 44 wherein said sheath removable cover for said sheath opening has a slotted top which can be turned with pressure applied thereto.

51. A method according to claim 27 wherein said support section is sized and shaped to fit so that said nozzle enters the desired said orifice of said body with said support section fitting into the appropriate portion of said body without projecting outward away from said body.

* * * * *